United States Patent
Yamamoto

(10) Patent No.: US 10,143,445 B2
(45) Date of Patent: Dec. 4, 2018

(54) ULTRASOUND DIAGNOSTIC APPARATUS AND ULTRASOUND DIAGNOSTIC IMAGE DATA PROCESSING METHOD

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 529 days.

(21) Appl. No.: 14/551,785

(22) Filed: Nov. 24, 2014

(65) Prior Publication Data

US 2015/0080733 A1 Mar. 19, 2015

Related U.S. Application Data

(63) Continuation of application No. PCT/JP2013/064460, filed on May 24, 2013.

(30) Foreign Application Priority Data

May 25, 2012 (JP) ................................ 2012-120010

(51) Int. Cl.
A61B 8/08 (2006.01)
A61B 8/14 (2006.01)
(Continued)

(52) U.S. Cl.
CPC .............. *A61B 8/5269* (2013.01); *A61B 8/14* (2013.01); *A61B 8/4488* (2013.01);
(Continued)

(58) Field of Classification Search
CPC .................................... A61B 8/00; G01S 7/00
See application file for complete search history.

(56) References Cited

U.S. PATENT DOCUMENTS 4,852,577 A * 8/1989 Smith ................. G01S 7/52049
600/443
6,305,225 B1 * 10/2001 Bae ..................... G01S 7/52046
600/447
(Continued)

FOREIGN PATENT DOCUMENTS

JP 2001-252276 A 9/2001
JP 2009-142680 A 7/2009

OTHER PUBLICATIONS

Nock, Levin, Gregg E. Trahey, and Stephen W. Smith. "Phase aberration correction in medical ultrasound using speckle brightness as a quality factor." The Journal of the Acoustical Society of America 85.5 (1989): 1819-1833.*
(Continued)

*Primary Examiner* — Luther G Behringer
*Assistant Examiner* — Sean D Mattson
(74) *Attorney, Agent, or Firm* — Birch, Stewart, Kolasch & Birch, LLP

(57) ABSTRACT

In this ultrasound diagnostic device and ultrasound diagnostic image data processing method, an element data determination unit compares a pre-set threshold value with the average value of the amplitude values in the element direction of the element data calculated by an average value calculation unit in the element direction, and an RF data calculation unit performs a process in which the element data of which the absolute value of the amplitude value is the maximum is adopted as the RF data without phasing addition when the average value (Aa) is greater than the threshold value. Meanwhile, when the average value (Ab) is equal to or lower than the threshold value, the RF data calculation unit performs a process in which the average values of all the amplitude values in the element direction of the element data are adopted as the RF data without phasing addition.

11 Claims, 10 Drawing Sheets

(51) Int. Cl.
*A61B 8/00* (2006.01)
*G01S 7/52* (2006.01)
*G01S 15/89* (2006.01)

(52) U.S. Cl.
CPC ........ *A61B 8/5207* (2013.01); *G01S 7/52049* (2013.01); *G01S 15/8915* (2013.01); *A61B 8/58* (2013.01)

(56) References Cited

U.S. PATENT DOCUMENTS

| | | | | |
|---|---|---|---|---|
| 2003/0092990 A1* | 5/2003 | Baba | ............ | A61B 8/00 600/443 |
| 2006/0122506 A1* | 6/2006 | Davies | ............ | A61B 8/14 600/437 |
| 2007/0083110 A1* | 4/2007 | Lin | ............ | A61B 8/08 600/437 |
| 2008/0229832 A1* | 9/2008 | Huang | ............ | A61B 8/13 73/620 |
| 2009/0093721 A1* | 4/2009 | Katsuyama | ............ | A61B 8/00 600/449 |

OTHER PUBLICATIONS

International Preliminary Report on Patentability and translation of the Written Opinion of the International Searching Authority (Forms PCT/IB/338, PCT/IB/373 and PCT/ISA/237), dated Dec. 4, 2014, in International Application No. PCT/JP2013/064460.
International Search Report, issued in PCT/JP2013/064460, dated Jun. 18, 2013.
Japanese Office Action, dated Oct. 13, 2015, for Japanese Application No. 2012-120010, along with a Partial English translation.

\* cited by examiner

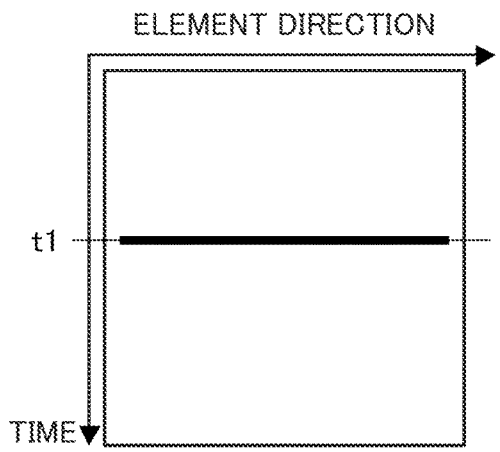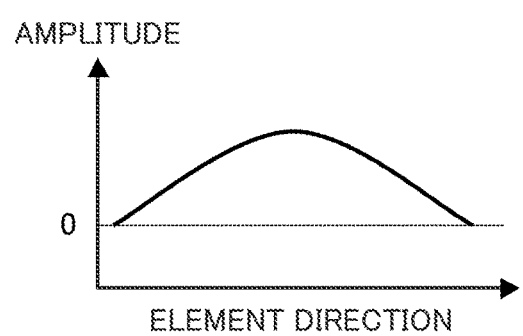
FIG. 3A  FIG. 3B
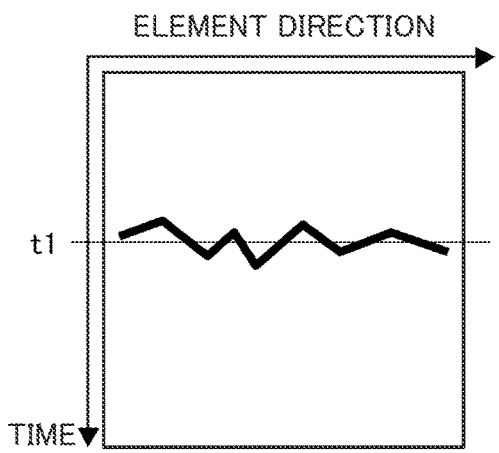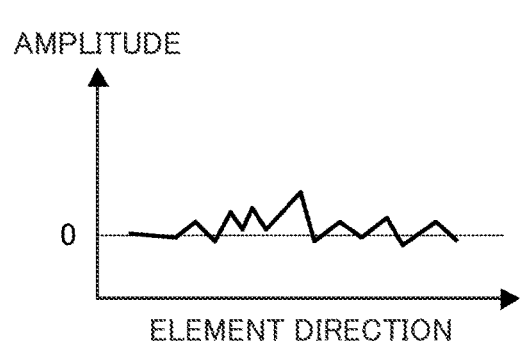
FIG. 3C  FIG. 3D

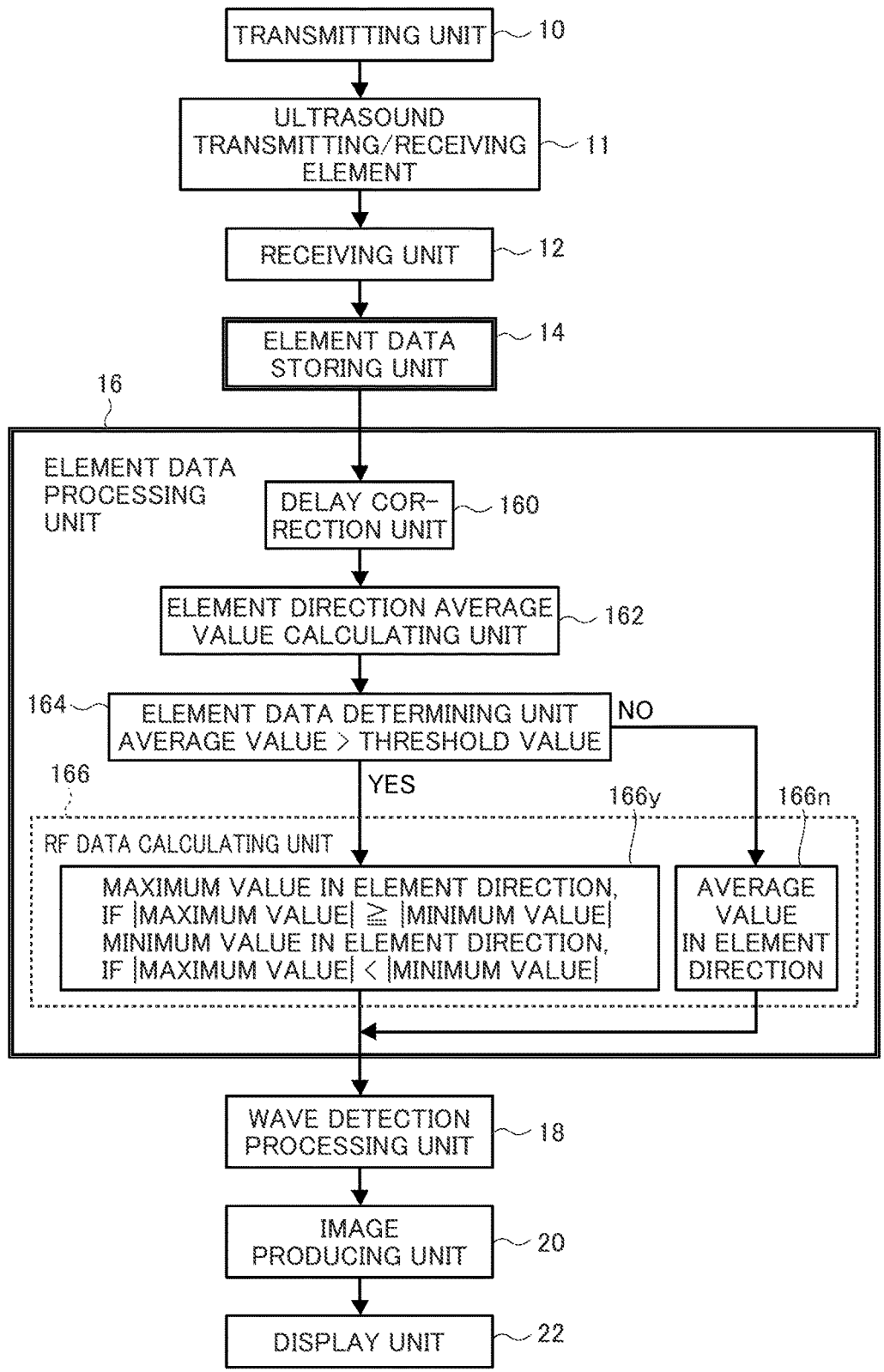

ULTRASOUND DIAGNOSTIC APPARATUS AND ULTRASOUND DIAGNOSTIC IMAGE DATA PROCESSING METHOD

CROSS-REFERENCE TO RELATED APPLICATIONS

This application is a Continuation of PCT International Application No. PCT/JP2013/064460 filed on May 24, 2013, which claims priority under 35 U.S.C. § 119(a) to Japanese Application No. 2012-120010 filed on May 25, 2012. Each of the above application(s) is hereby expressly incorporated by reference, in its entirety, into the present application.

BACKGROUND OF THE INVENTION

The present invention relates to an ultrasound diagnostic apparatus and an ultrasound diagnostic image data processing method, and in particular, to an ultrasound diagnostic apparatus and an ultrasound diagnostic image data processing method for photographing and displaying an ultrasound image of a subject by using an ultrasonic wave.

In the field of medicine, ultrasound diagnostic apparatuses are widely used for diagnostics and inspections. An ultrasound diagnostic apparatus irradiates an ultrasonic wave to a subject through an ultrasound probe and produces a tomographic image (hereinafter referred to as ultrasound image) of the subject from its echo (reflection) signal.

In order to improve the focus of such ultrasound image, various approaches are proposed. For example, in JP 2009-142680 A, as shown in a block diagram of FIG. 11, when a switching interval of a reception wave delay correction value is set, a phasing adder part 3 can perform reception wave focus operation immediately, according to the set switching interval. A plurality of optimum values for the switching interval of a reception wave delay correction value, per site to be observed and/or per body type of the subject, are prepared in a focus switching interval storing part 7 so that in case a satisfactory level of focus is not attained within the presumed standard sonic speeds due to difference in body type of the subject, or difference in ultrasonic wave beam path to the site to be observed, the reception wave delay correction value switching interval can be reset to a different value.

SUMMARY OF THE INVENTION

However, in JP 2009-142680 A, even if a plurality of setting values are prepared, there is a problem in that, it is difficult to adjust to an optimum focus, because if the quality of the reception signal processed in an ultrasound transmitting/receiving unit 2 is degraded due to much noise, the quality of the element data obtained by processing the reception signal is also degraded, and brightness is degraded by performing phasing addition on the partially or entirely phase-shifted element data. In addition, since the element data is not stored, new B-mode image data is not produced after the wave receiving delay correction value switching interval is changed, until an ultrasonic pulse is re-transmitted into the subject.

The present invention has been done in consideration of the above-described issues, and a first object of the invention is to provide an ultrasound diagnostic apparatus and an ultrasound diagnostic image data processing method, in which, after performing delay correction to the element data which is obtained by A/D (analog/digital)-converting an echo signal, the quality of the element data which is susceptible to a noise in the element data is determined based on the element data without phasing addition, and different processes in response to the determination result are performed on the element data, so that an ultrasound image with a preferred S/N (signal/noise) can be displayed.

A second object of the present invention is to provide an ultrasound diagnostic apparatus and an ultrasound diagnostic image data processing method, in which an element data storing unit stores the element data, so that new B mode image data after the sonic speed setting value is changed can be produced by using the stored element data, without re-transmitting an ultrasonic pulse into the subject by a transmitting unit.

A third object of the present invention is to provide an ultrasound diagnostic apparatus and an ultrasound diagnostic image data processing method, in which a procedure of producing new B mode image data after the sonic speed setting value is changed, is automatically repeated until predetermined image quality criteria is satisfied, so that an ultrasound image adjusted to an optimum focus can be displayed.

To attain the above objects, a first embodiment of the present invention provides an ultrasound diagnostic apparatus, comprising: an ultrasound transmitting/receiving unit which transmits ultrasonic pulses to a subject by using a plurality of ultrasound transmitting/receiving elements arranged in one direction, and receives an ultrasonic echo that is the ultrasonic pulse reflected by the subject, to produce element data; an element data storing unit which stores the element data produced by the ultrasound transmitting/receiving unit; a delay correction unit which corrects a delay time of the plurality of ultrasound transmitting/receiving elements in an arranging direction thereof by using a predetermined sonic speed setting value, to perform phasing on the element data, the delay time being an arrival time difference of the ultrasonic echo in the element data read out from the element data storing unit; an element data determining unit which determines the quality of the element data, based on the element data after correction of the delay time of the plurality of ultrasound transmitting/receiving elements in the arranging direction thereof, the quality of the element data being susceptible to a noise in the element data; and an image producing unit which produces an ultrasound image, by performing different processes on the element data in response to a determination result from the element data determining unit.

In the first embodiment, preferably, the image producing unit performs different processes on the element data depending on whether the element data is of high quality with the noise reduced, or of low quality due to influence of the noise, in response to a determination result from the element data determining unit.

Preferably, the element data determining unit determines the quality of the element data based on a distribution of amplitude values of the element data after correction of the delay time of the plurality of ultrasound transmitting/receiving elements in the arranging direction thereof.

Preferably, the element data determining unit compares an average value of amplitude values of the element data after correction of the delay time of the plurality of ultrasound transmitting/receiving elements in the arranging direction thereof, with a threshold value predetermined in response to the noise, and if the average value is greater than the threshold value, the element data determining unit determines that the element data is of high quality with the noise reduced, or if the average value is equal to or lower than the threshold value, the element data determining unit determines that the element data is of low quality due to influence of the noise.

Preferably, the image producing unit performs a process on the element data in which an absolute value of the amplitude value is a maximum value, if the element data determining unit determines that the element data is of high quality, and performs a process on the average value of all the amplitude values of the element data after correction of the delay time of the plurality of ultrasound transmitting/receiving elements in the arranging direction thereof, if the element data determining unit determines that the element data is of low quality.

Preferably, the ultrasound diagnostic apparatus further comprises an image quality determining unit which determines the image quality of the ultrasound image produced by the image producing unit, in response to an amount of image features of the ultrasound image.

Preferably, the image quality determining unit determines the image quality of the ultrasound image produced by the image producing unit, on the basis of a brightness value of the ultrasound image.

Preferably, the image quality determining unit determines the image quality of the ultrasound image produced by the image producing unit, on the basis of a sharpness value of the ultrasound image.

Preferably, the image quality determining unit determines the image quality of the ultrasound image produced by the image producing unit, in response to whether the amount of image features is equal to or greater than a threshold value corresponding to a predetermined level of image quality of an ultrasound image, or not.

Preferably, the ultrasound diagnostic apparatus further comprises a process condition changing unit, which changes the sonic speed setting value if the image quality determining unit determines that the ultrasound image produced by the image producing unit does not have predetermined image quality, wherein, if the image quality determining unit determines that the ultrasound image produced by the image producing unit does not have predetermined image quality, changing the sonic speed setting value by the process condition changing unit, correcting the delay time of the element data by the delay correction unit, determining the quality of the element data by the element data determining unit, producing the ultrasound image by the image producing unit, and determining the image quality of the ultrasound image by the image quality determining unit are controlled to be repeated, until the image quality determining unit determines that the ultrasound image has the predetermined image quality.

A second embodiment of the present invention provides an ultrasound diagnostic image data processing method, comprising: a first step of producing an element data by transmitting an ultrasonic pulse from a plurality of ultrasound transmitting/receiving elements arranged in one direction to a subject, and receiving an ultrasonic echo which is the ultrasonic pulse transmitted and reflected by the subject by the plurality of ultrasound transmitting/receiving elements; a second step of storing the element data produced in the first step in an element data storing unit; a third step of correcting a delay time of the plurality of ultrasound transmitting/receiving elements in an arranging direction thereof, by using a predetermined sonic speed setting value to perform phasing on the element data, the delay time being an arrival time difference of the ultrasonic echo in the element data read out from the element data storing unit; a fourth step of determining the quality of the element data which is susceptible to a noise in the element data, based on the element data after correction of the delay time of the plurality of ultrasound transmitting/receiving elements in the arranging direction thereof; and a fifth step of producing an ultrasound image by performing different processes on the element data, in response to a determination result of the element data quality in the fourth step.

In the second embodiment, preferably, the ultrasound diagnostic image data processing method further comprises: a sixth step of determining the image quality of the ultrasound image produced in the fifth step, in response to an amount of image features of the ultrasound image; and a seventh step of changing the sonic speed setting value if the ultrasound image produced in the fifth step is determined not to be of predetermined image quality in the sixth step, wherein, if the ultrasound image is determined not to be of predetermined image quality, changing the sonic speed setting value in the seventh step, correcting the delay time of the element data in the third step, determining the quality of the element data in the fourth step, producing the ultrasound image in the fifth step, and determining the image quality of the ultrasound image in the sixth step are controlled to be repeated, until the ultrasound image is determined to be of the predetermined image quality.

According to the present invention, after performing delay correction to the element data which is obtained by A/D (analog/digital)-converting an echo signal, the quality of the element data susceptible to a noise in the element data is determined based on the element data without phasing addition, and different processes in response to the determination result are performed on the element data, so that an ultrasound image with a preferred S/N (signal/noise) can be produced.

In addition, according to the present invention, an element data storing unit stores the element data, so that new B mode image data after the sonic speed setting value is changed can be produced by using the stored element data, without re-transmitting an ultrasonic pulse into the subject by a transmitting unit.

Further, according to the present invention, a procedure of producing new B mode image data after the sonic speed setting value is changed, is automatically repeated until the predetermined image quality criteria is satisfied, so that an ultrasound image adjusted to an optimum focus can be displayed.

BRIEF DESCRIPTION OF THE DRAWINGS

FIGS. 3A and 3B are explanatory diagrams showing high quality element data with low noise. FIG. 3A shows the element data after delay correction, and FIG. 3B shows a distribution of amplitude values in the element direction of the element data at a time t1 at which a high brightness signal is displayed. FIGS. 3C and 3D are explanatory diagrams showing low quality element data for which delay correction did not function properly due to influence of the noise. FIG. 3C shows the element data after delay correction, and FIG. 3D shows a distribution of amplitude values in the element direction of the element data at a time t1 at which a high brightness signal is displayed.

FIG. 5 is a functional block diagram showing Embodiment 1 of the ultrasound diagnostic apparatus shown in FIGS. 1 and 2.

DETAILED DESCRIPTION OF THE INVENTION

Hereinafter, an ultrasound diagnostic apparatus according to the present invention will be described in detail on the basis of preferred embodiments shown in the accompanying drawings.

Figure 1:
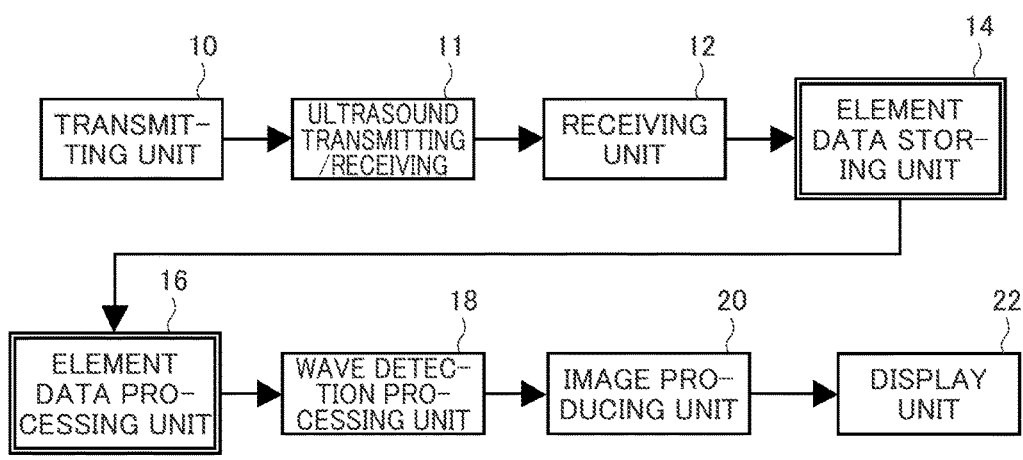
FIG. 1 is a functional block diagram showing one embodiment of an ultrasound diagnostic apparatus according to the present invention.

FIG. 1 is a functional block diagram showing one embodiment of an ultrasound diagnostic apparatus according to the present invention. The ultrasound diagnostic apparatus shown in FIG. 1 includes a transmitting unit 10, an ultrasound transmitting/receiving element 11, a receiving unit 12, an element data storing unit 14, an element data processing unit 16, a wave detection processing unit 18, an image producing unit 20, and a display unit 22.

The transmitting unit 10 produces an ultrasonic pulse (ultrasonic wave beam) by driving a plurality of ultrasound transmitting/receiving elements (piezoelectric elements) 11 arranged in one direction of an ultrasound probe (not shown) which, in use, is abutted to a diagnostic site of a subject.

The ultrasound probe transmits the ultrasonic pulse produced by the transmitting unit 10 into the subject using the ultrasound transmitting/receiving elements 11, receives a reflection echo signal (ultrasonic echo) which is the ultrasonic pulse reflected by the subject, and converts the reflection echo signal into an electrical signal (analog).

The receiving unit 12 amplifies the electrical signal of the reflection echo signal which is received and converted by the ultrasound probe, filters out high frequency components with a low-pass filter, and performs A/D conversion to produce element data (digital). That is, the element data is the data (digital) obtained by amplifying, filtering, and A/D-converting the electrical signal (analog) of the reflection echo signal (ultrasonic echo) received by the ultrasound probe.

The transmitting unit 10, the ultrasound probe, and the receiving unit 12 described above constitute the ultrasound transmitting/receiving unit of the present invention.

The element data storing unit 14 stores the element data output by the receiving unit 12. The stored element data is retained until it is deleted by a predetermined process in order to change the sonic speed setting value used in a first delay correction to a different sonic speed setting value for recalculation.

Figure 2:
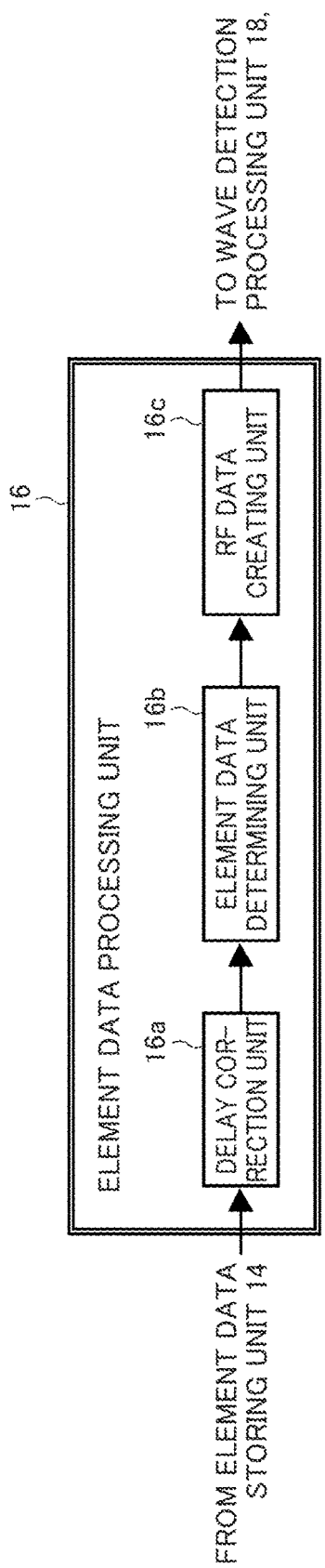
FIG. 2 is a functional block diagram showing a detailed configuration of an element data processing unit of the ultrasound diagnostic apparatus shown in FIG. 1.

FIG. 2 is a functional block diagram showing a detailed configuration of an element data processing unit of the ultrasound diagnostic apparatus shown in FIG. 1. The element data processing unit 16, as shown in FIG. 2, includes a delay correction unit 16a which corrects delay time in the element direction (i.e., in the arranging direction of the ultrasound transmitting/receiving elements 11 arranged in one direction) of the element data stored in the element data storing unit 14, an element data determining unit 16b which determines the quality of the element data susceptible to a noise in the element data, on the basis of the distribution of the amplitude values in the element direction of the element data after delay correction, and an RF data creating unit 16c which performs different processes on the element data depending on the determination result whether the element data is of high quality with low noise, or the element data is of low quality due to influence of the noise. In the ultrasound diagnostic apparatus shown in the prior art, the RF (radio frequency) data is the data obtained through delay correction and phasing addition of the element data. In the ultrasound diagnostic apparatus according to the present invention, the RF (radio frequency) data is the data obtained by performing different processes on the element data according to whether the element data is of high quality (low noise) or the element data is of low quality (due to influence of the noise) based on the determination of the quality of the element data on the basis of the distribution of the amplitude values in the element direction of the element data, the element data being obtained through delay correction and without performing phasing addition.

The delay correction unit 16a performs delay correction process to the element data provided by (or read out from) the element data storing unit 14, using a predetermined sonic speed setting value. Specifically, the delay correction process is to correct the delay time in the element direction of the element data, which is the arrival time difference of the ultrasonic echo of the element, and to perform phase correction on the element data.

FIGS. 3A and 3B are explanatory diagrams showing high quality element data with low noise. FIG. 3A shows element data after delay correction with the horizontal axis being element direction and the vertical axis being time. FIG. 3B shows the distribution of the amplitude values in the element direction of the element data at a time t1 at which a high brightness signal is displayed, with the horizontal axis being element direction, and the vertical axis being amplitude. The element data, in this case, is straight with no influence of the noise in the element direction at a time t1, as shown in FIG. 3A, and at the time t1, the amplitude values become high in the vicinity of the center of the element, and decrease towards the ends of the element, as shown in FIG. 3B. In addition, although the amplitude values in the element direction of the element at the time t1 shown in FIG. 3B are distributed in the positive region, amplitude values at a different time may be distributed in the negative region, because the element data moves back and forth over time between the positive region and the negative region.

On the other hand, FIGS. 3C and 3D are explanatory diagrams showing low quality element data for which delay correction did not function properly due to influence of the noise. FIG. 3C shows the element data after delay correction, with the horizontal axis being element direction, and the vertical axis being time, and FIG. 3D shows the distribution of the amplitude values in the element direction of the element data at a time t1 at which a high brightness signal is displayed, with the horizontal axis being element direction, and the vertical axis being amplitude. The element data, in this case, as shown in FIG. 3C, is not straight but fluctuates finely due to influence of the noise at the time t1, and amplitude values in the element direction at the time t1 are not distributed in a smooth shape, but are distributed in various sizes as shown in FIG. 3D.

The element data determining unit 16b determines the quality of the element data susceptible to a noise in the element data, on the basis of the distribution of the amplitude values of the element data after delay correction in the element direction. Specifically, the element data determining unit 16b performs a process to determine whether the element data is of high quality as shown in FIGS. 3A and 3B, or the element data is of low quality as shown in FIGS. 3C and 3D. The element data determining unit 16b, in this embodiment, compares an average value of all the amplitude values in the element direction of the element data, with a threshold value predetermined in response to a noise. If the average value is higher than the threshold value, the element data is determined to be of high quality with low noise, and if the average value is equal to or lower than the threshold value, the element data is determined to be of low quality due to influence of the noise. It should be noted that the element data determining unit 16b determines the quality of the element data based on the element data after delay correction in the element direction, and it is optional to determine the quality of the element data on the basis of the distribution of the amplitude values of the element data. Methods for determining the quality of the element data are not limited.

In response to the determination result by the element data determining unit 16b, the RF data creating unit 16c creates RF data by performing different processes on the element data depending on whether the element data is of high quality, or the element data is of low quality. Specifically, when the element data is determined to be of high quality by the element data determining unit 16b, the RF data creating unit 16c adopts as the RF data, for example, the element data having the maximum absolute value of the amplitude value, so that the element data of the highest quality can be selected out of the reflection echo signals with low noise. On the other hand, when the element data is determined to be of low quality, the RF data creating unit 16c adopts as the RF data an average value of all the amplitude values in the element direction of the element data so that a noise in the reflection echo signal can be suppressed. In this way, S/N can be improved by selecting the element data of highest quality among the element data with low noise, and by obtaining an average value of the element data affected by noise, as the RF data value.

It should be noted that the RF data creating unit 16c performs different processes on the element data in response to the determination result by the element data determining unit 16b, and it is optional to perform different processes on the element data depending on whether the element data is of high quality or the element data is of low quality.

For the element data at a time other than t1, the quality of the element data is determined similarly on the basis of the distribution of the amplitude values in the element direction of the element data after performing delay correction to the element data, and different processes are performed on the element data depending on whether the element data is of high quality or the element data is of low quality, so that the RF data from the time zero to a predetermined time can be created.

Subsequently, the wave detection processing unit 18 shown in FIG. 1 produces an envelope signal by performing an envelope wave detection process with a low-pass filter or the like, on the RF data created by the RF data creating unit 16c, after correcting the attenuation due to distance, in response to the depth of the reflecting position of the ultrasonic wave by STC (Sensitivity Time Gain Control).

The image producing unit 20 produces image data by performing processes such as logarithm compression, gain adjustment on the envelope signal produced by the wave detection processing unit 18, and converting (raster-converting) the image data into image data conforming to a scan mode for common television signals, so that B-mode image data having brightness information according to the signal strength of the echo can be produced.

The RF data creating unit 16c, the wave detection processing unit 18, and the image producing unit 20 constitute the image producing unit of the present invention.

The display unit 22 displays an ultrasound image corresponding to the B-mode image data created by the image producing unit 20.

The ultrasound diagnostic apparatus according to the present invention is basically configured as described above.

Next, the operation of the ultrasound diagnostic apparatus and the ultrasound diagnostic image data processing method according to the present invention will be described.

Figure 4:
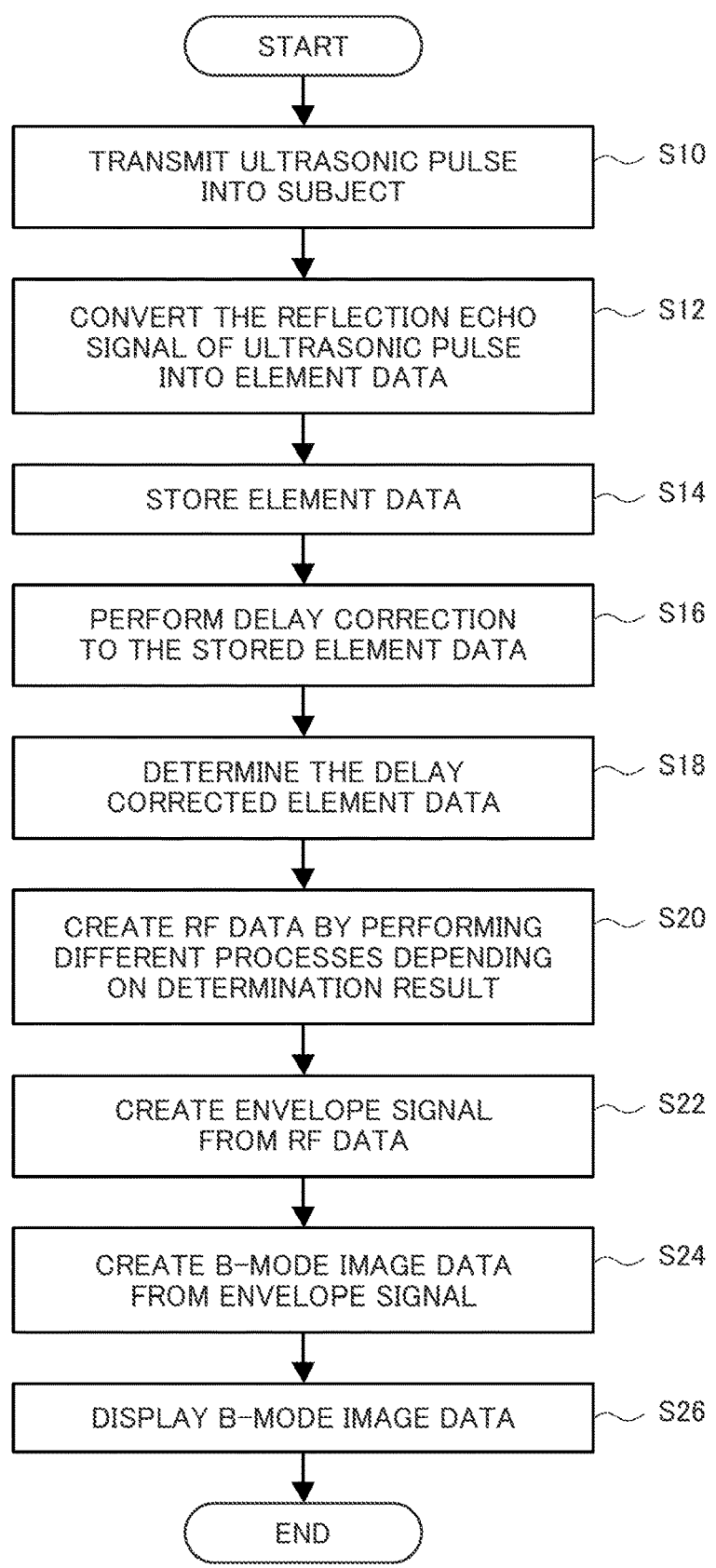
FIG. 4 is a flowchart showing one embodiment of a procedure of an ultrasound diagnostic image data processing method according to the present invention.

FIG. 4 is a flowchart showing one embodiment of a procedure of an ultrasound diagnostic image data processing method according to the present invention. The invention is to provide an ultrasound diagnostic image data processing method in which, after performing delay correction to the element data which is obtained by A/D (analog/digital)-converting an echo signal, the quality of the element data is determined based on the element data without phasing addition, and different processes in response to the determination result are performed on the element data, so that an ultrasound image with a preferred S/N (signal/noise) can be displayed. In addition, the present invention provides an ultrasound diagnostic image data processing method in which an element data storing unit stores the element data, so that new B mode image data after the sonic speed setting value is changed can be produced by using the stored element data, without re-transmitting an ultrasonic pulse into the subject. The method is constituted of Steps S10-S26.

In Step S10, the transmitting unit 10 drives a plurality of ultrasound transmitting/receiving elements 11 arranged in one direction of an ultrasound probe to produce an ultrasonic pulse, and the ultrasound probe transmits the ultrasonic pulse into the subject by using the ultrasound transmitting/receiving elements 11.

In Step S12, the ultrasound probe uses the ultrasound transmitting/receiving elements 11 to receive an reflection echo signal (ultrasonic echo) which is the ultrasonic pulse transmitted into the subject in Step S10 and is reflected by the subject, and covert the reflection echo signal into an electrical signal (analog). The receiving unit 12 amplifies, filters, and A/D-converts the electrical signal of the reflection echo signal of the ultrasonic pulse received and converted by the ultrasound probe to produce the element data.

In Step S14, the element data storing unit 14 stores the element data output in Step S12.

In Step S16, the delay correction unit 16a of the element data processing unit 16 reads out the element data stored in Step S14, from the element data storing unit 14, and performs a delay correction process by using a predetermined sonic speed setting value. Specifically, the delay correction process is to correct the delay time in the element direction of the element data, which is the arrival time difference of the ultrasonic echo of the element data, and to perform phasing on the element data.

In Step S18, the element data determining unit 16b determines whether the quality of the element data susceptible to a noise in the element data is of high quality with low noise or of low quality with high noise, on the basis of the distribution of the amplitude values in the element direction at a time t1, of the element data for which delay correction has been performed in Step S16.

In Step S20, the RF data creating unit 16c creates the RF data by performing different processes on the element data depending on whether the element data is of high quality or of low quality, in response to the determination result provided in Step S18. For the element data at a time other than t1, Steps S16-S20 are repeated so as to create the RF data from the time zero to a predetermined time.

In Step S22, the wave detection processing unit 18 produces an envelope signal from the RF data created in Step S20.

In Step S24, the image producing unit 20 produces B-mode image data from the envelope signal created in Step S22.

In Step S26, the display unit 22 displays an ultrasound image corresponding to the B-mode image data created in Step S24.

The ultrasound diagnostic image data processing method according to the present invention is basically configured by the steps described above.

Embodiment 1

First, Embodiment 1 of the ultrasound diagnostic apparatus according to the present invention will be described.

Figure 6A:
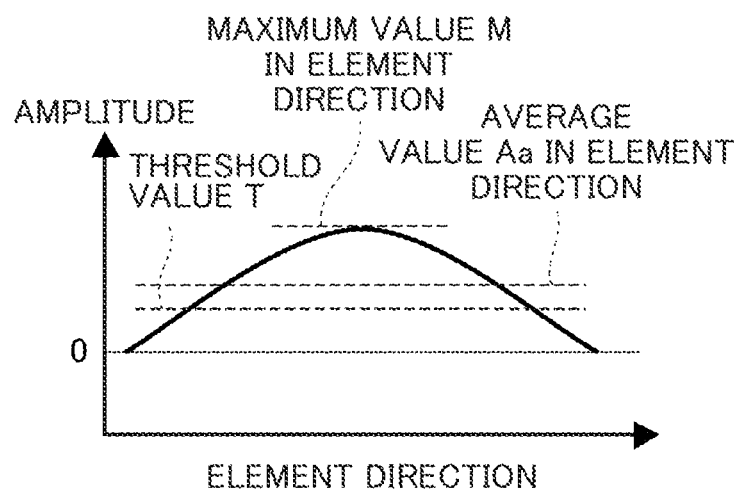
FIG. 6A is an explanatory diagram illustrating a process content for the high quality element data with low noise.
Figure 6B:
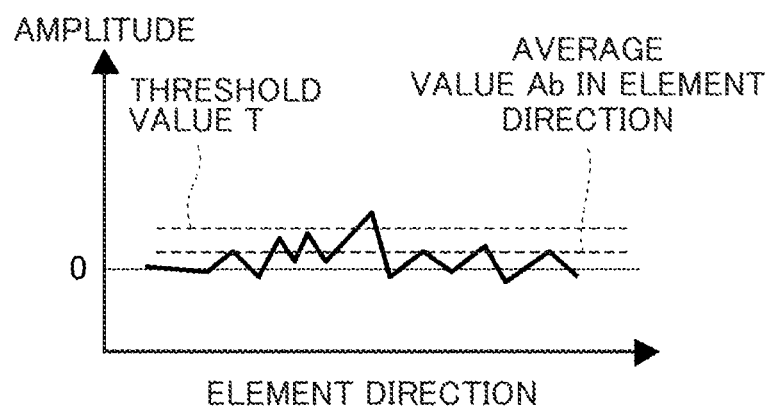
FIG. 6B is an explanatory diagram illustrating a process content for the low quality element data for which delay correction did not function properly due to influence of the noise.

FIG. 5 is a functional block diagram showing Embodiment 1 of the ultrasound diagnostic apparatus shown in FIGS. 1 and 2. FIG. 6A is an explanatory diagram illustrating a process content for the high quality element data with low noise, and FIG. 6B is an explanatory diagram illustrating a process content for the low quality element data to which delay correction did not function properly due to influence of the noise. Embodiment 1 shows the process content in respective components of the element data processing unit 16 shown in FIG. 2, in more detail.

Other parts are the same as the embodiment of the ultrasound diagnostic apparatus according to the present invention shown in FIG. 1.

A delay correction unit 160 corresponds to the delay correction unit 16a in FIG. 2, and performs delay correction to the element data stored in the element data storing unit 14.

An element-direction average value calculating unit 162 and an element data determining unit 164 correspond to the element data determining unit 16b in FIG. 2.

The element-direction average value calculating unit 162 calculates an average value A of the amplitude values in the element direction of the element data for which correction has been performed by the delay correction unit 160. In the following description, the average value for the high quality element data shown in FIG. 6A, and the average value for the low quality element data shown FIG. 6B will be called as Aa and Ab, respectively.

The element data determining unit 164 compares the average value A of the amplitude values in the element direction of the element data calculated by the element-direction average value calculating unit 162 with a predetermined threshold value T. Then, as shown in FIG. 6A, if the average value A (Aa) is greater than the threshold value T (YES), the element data determining unit 164 determines that the element data is of high quality with low noise, and an RF data calculating unit 166 performs a subsequently described Process 166y which relates to high quality element data. On the other hand, as shown in FIG. 6B, when the average value A (Ab) is equal to or lower than the threshold value T (NO), the element data determining unit 164 determines that the element data is of low quality with high noise, and the RF data calculating unit 166 performs a subsequently described Process 166n which relates to low quality element data.

The RF data calculating unit 166 corresponds to the RF data creating unit 16c in FIG. 2, and in response to the determination result, performs either one of two processes of Process 166y and Process 166n on the element data determined by the element data determining unit 164. Process 166y is a process to adopt the element data having the maximum absolute value of the amplitude value, without phasing addition, as the RE data. Specifically, as shown in FIG. 6A, out of the amplitude values in the element direction of the element data at time t1, the absolute value of the maximum value and the absolute value of the minimum value are compared. If |maximum value| is equal to or greater than |minimum value|, the maximum value (M in FIG. 6A) of the amplitude values in the element direction of the element data at a time t1 is adopted as the RF data value, and if |maximum value| is less than |minimum value|, the minimum value of the amplitude values in the element direction of the element data at a time t1 is adopted as the RF data value. On the other hand, Process 166n is a process to adopt the average value of all the amplitude values in the element direction of the element data without phasing addition, as the RF data. Specifically, as shown in FIG. 6B, the average value of all the amplitude values in the element direction of the element data at a time t1 (Ab in FIG. 6B) is adopted as the RF data value. Alternately, the average value may be a value already calculated by the element-direction average value calculating unit 162.

Similarly, for the element data at a time other than t1, after performing delay correction to the element data, an average value of the amplitude values in the element direction of the element data is calculated, and the calculated average value is compared with the predetermined threshold value. In response to a determination result, either one of Process 166y and Process 166n is performed to create the RF data from the time zero to a predetermined time.

The ultrasound diagnostic apparatus of Embodiment 1 provides an effect in which, after performing delay correction to the element data which is obtained by A/D (analog/digital)-converting an echo signal, the quality of the element data is determined based on the element data without phasing addition, and different processes in response to the determination result are performed on the element data, so that an ultrasound image with a preferred S/N (signal/noise) can be displayed. In addition, the ultrasound diagnostic apparatus of Embodiment 1 also provides an effect in which an element data storing unit stores the element data, so that by using the stored element data, new B mode image data after the sonic speed setting value is changed can be produced without re-transmitting an ultrasonic pulse into the subject by the transmitting unit 10.

Embodiment 1 of the ultrasound diagnostic apparatus according to the present invention, is basically configured as described above.

Next, the operation of the ultrasound diagnostic apparatus according to the present invention, and the operation of Embodiment 1 of the ultrasound diagnostic image data processing method will be described.

Figure 7:
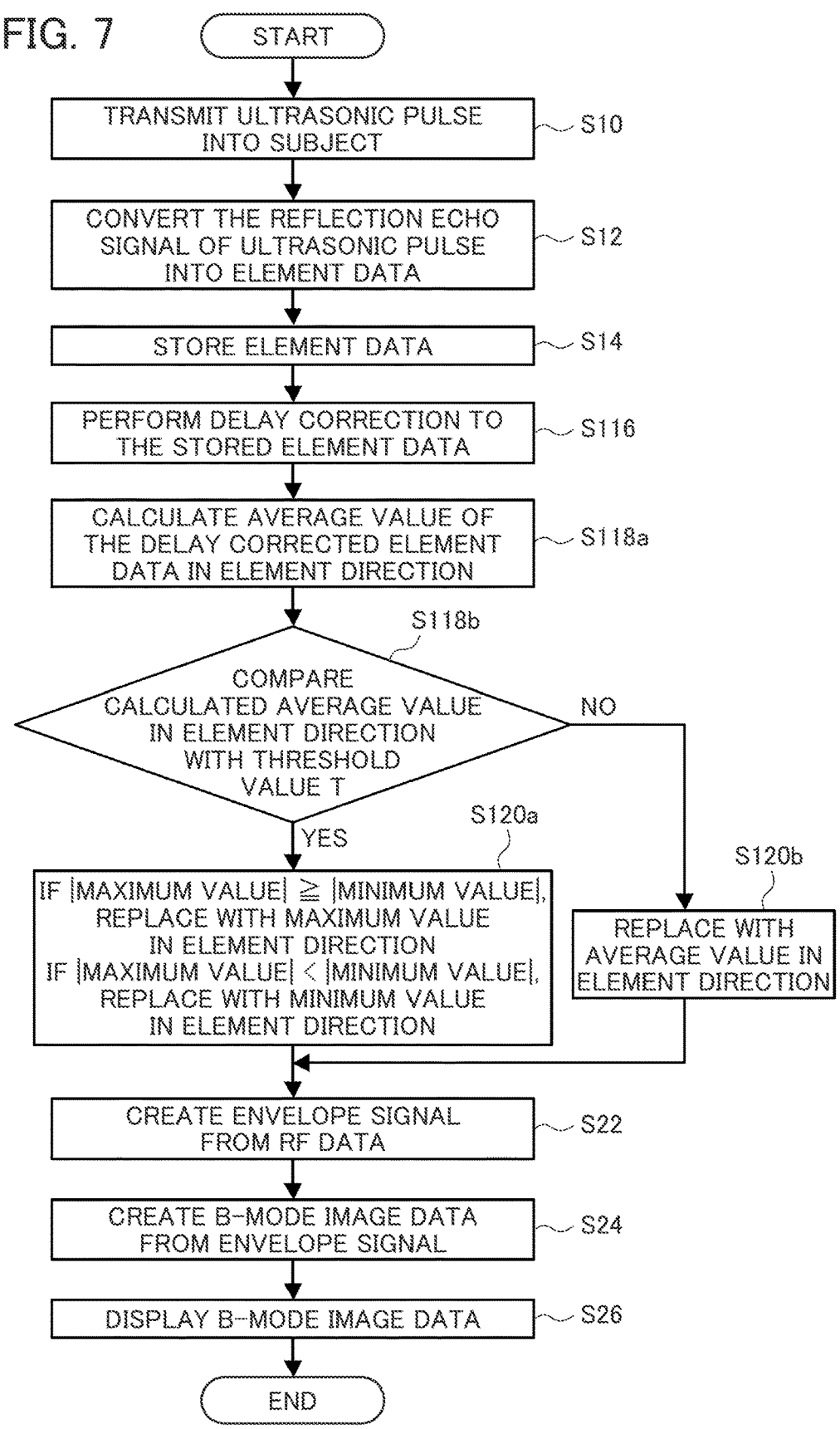
FIG. 7 is a flowchart showing Embodiment 1 of a procedure of an ultrasound diagnostic image data processing method according to the present invention.

FIG. 7 is a flowchart showing Embodiment 1 of a procedure of an ultrasound diagnostic image data processing method. Embodiment 1 shows the process content in Steps S16-S20 shown in FIG. 4 in more detail.

Other parts are the same as the embodiment of the ultrasound diagnostic image data processing method according to the present invention, shown in FIG. 4.

In Step S116, the delay correction unit 160 performs delay correction to the element data stored in Step S14.

In Step S118a, the element-direction average value calculating unit 162 calculates an average values of the amplitude values in the element direction of the element data for which delay correction has been performed in Step S116.

In Step S118b, the element data determining unit 164 compares the average value of the amplitude values in the element direction of the element data calculated in Step S118a, with the threshold value T.

In Step S120a, when comparison by the element data determining unit 164 in Step S118b shows that the average value of the amplitude values in the element direction of the element data is greater than the threshold value T, the RF data calculating unit 166 compares the absolute value of the maximum value of the amplitude values in the element direction of the element data at a time t1 with the absolute value of the minimum value of the amplitude values in the element direction of the element data at a time t1. If |maximum value| is equal to or greater than |minimum value|, the maximum value of the amplitude values in the element direction of the element data at a time t1 is adopted as the RF data value, and if |maximum value| is less than |minimum value|, the minimum value of the amplitude values in the element direction of the element data is adopted as the RF data value.

In Step S120b, when comparison by the element data determining unit 164 in Step S118b shows that the average value of the amplitude values in the element direction of the element data is equal to or lower than the threshold value T, the RF data calculating unit 166 adopts the average value of all the amplitude values in the element direction of the element data at a time t1, as the RF data value.

Embodiment 1 of the ultrasound diagnostic image data processing method according to the present invention is basically configured by the above described steps.

Embodiment 2

Next, Embodiment 2 of the ultrasound diagnostic apparatus according to the present invention will be described.

Figure 8:
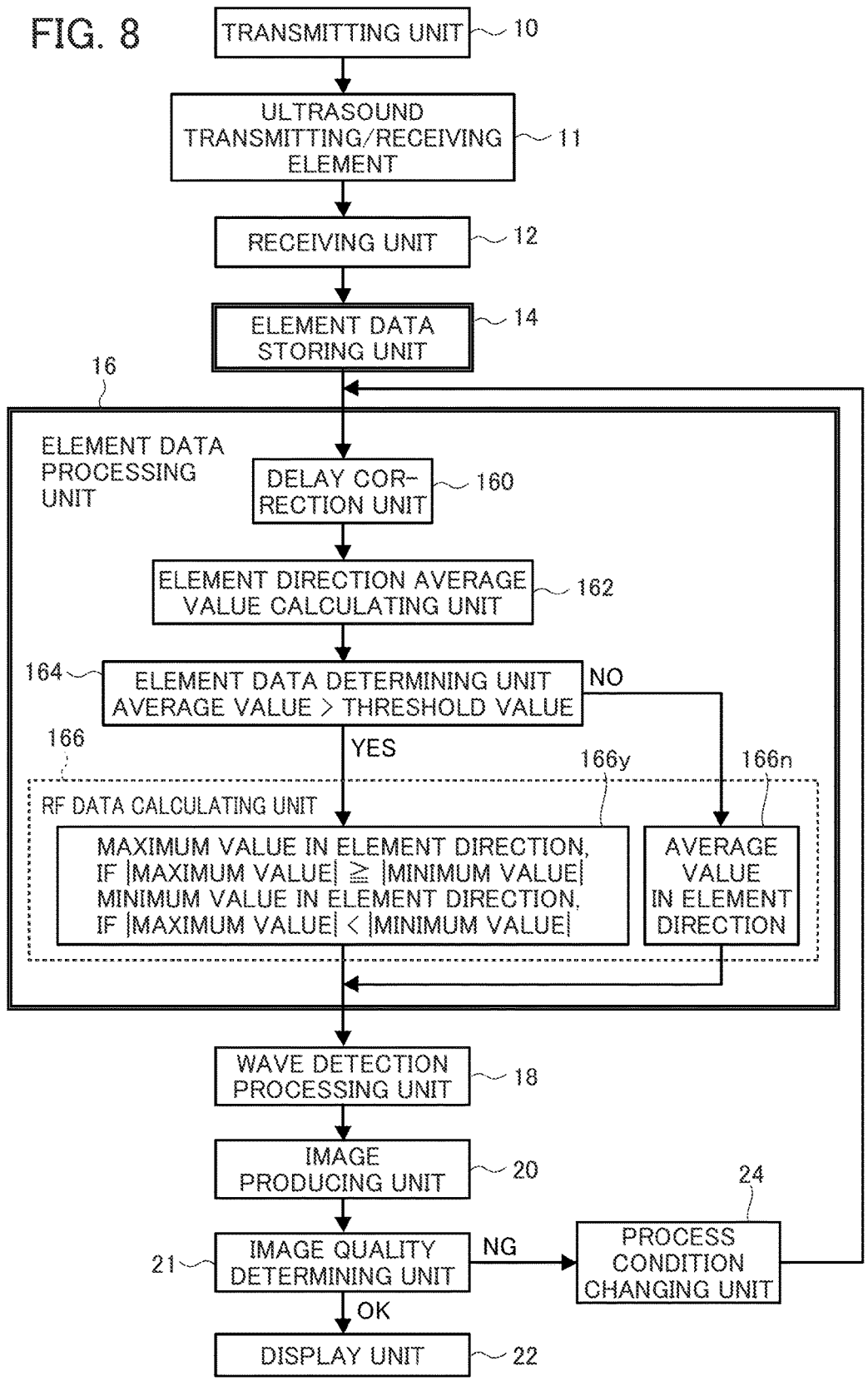
FIG. 8 is a functional block diagram showing Embodiment 2 of the ultrasound diagnostic apparatus shown in FIGS. 1 and 2.

FIG. 8 is a functional block diagram showing Embodiment 2 of the ultrasound diagnostic apparatus shown in FIGS. 1 and 2. Embodiment 2 additionally includes an image quality determining unit 21 between the image producing unit 20 and the display unit 22 in the functional block diagram showing Embodiment 1 of the ultrasound diagnostic apparatus shown in FIG. 5. If the determination result is "OK", the process proceeds to the display unit 22 same as in Embodiment 1. If the determination result shows "NG", the process returns to the delay correction unit 160 in Embodiment 1 through the process condition changing unit 24.

Other parts are the same as Embodiment 1 of the procedure of the process method of the ultrasound diagnostic apparatus, shown in FIG. 5.

The image quality determining unit 21 determines whether the image quality of the B-mode image data created by the image producing unit 20 satisfies the predetermined image quality criteria or not, in response to the amount of image features of the ultrasound image. If the image quality satisfies the image quality criteria, the process of display unit 22 is performed on the determined B-mode image data. If the image quality does not satisfy the image quality criteria, the process of the process condition changing unit 24 is performed.

The image quality determining unit 21 can determine the image quality in response to whether or not an amount of image features such as brightness, sharpness, on the ultrasound image corresponding to the B-mode image data created by the image producing unit 20 is equal to or higher than the threshold values predetermined for the amount of features such as brightness, sharpness, corresponding to a certain quality ultrasound image. In addition, for example, each time a different sonic speed setting value is applied, the difference in sonic speed setting values is calculated and a threshold value indicating a degree of convergence of the sonic speed setting value predetermined to the difference may be used as the image quality criteria.

The process condition changing unit 24 changes the sonic speed setting value currently set to a different sonic speed setting value, when the ultrasound image is determined by the image quality determining unit 21, to be of lower than the predetermined image quality corresponding to the B-mode image data created by the image producing unit 20. And in this case in which the ultrasound image is determined to be of lower quality, a series of procedures including, changing sonic speed setting value by the process condition changing unit 24, delay time correction of the element data by the delay correction unit 160, determining the quality of the element data by the element data determining unit (element-direction average value calculating unit 162 and the element data determining unit 164), creating an ultrasound image by the image producing unit (RF data calculating unit 166, wave detection processing unit 18, and image producing unit 20), and determining the image quality of the ultrasound image by the image quality determining unit 21 is controlled to be repeated until the ultrasound image corresponding to the B-mode image data created by the image producing unit 20 is determined to be of the predetermined image quality. Methods for changing the sonic speed setting value include for example, a method in which the delay correction unit 160 initially sets a most frequently used sonic speed setting value and the process condition changing unit 24 adds or subtracts a sonic speed difference predetermined for the sonic speed setting value from the initial value each time. Alternatively, for example, the delay correction unit 160 may set initially the sonic speed setting value previously used, and the process condition changing unit 24 adds or subtracts from the value by a sonic speed difference.

The ultrasound diagnostic apparatus of Embodiment 2 provides, in addition to the effect of Embodiment 1, an effect in which a procedure of producing new B mode image data after the sonic speed setting value is changed, is automatically repeated until the predetermined image quality criteria is satisfied, so that an ultrasound image adjusted to an optimum focus can be displayed.

Embodiment 2 of the ultrasound diagnostic apparatus according to the present invention is basically configured as described above.

Next, the operation of the ultrasound diagnostic apparatus, and the operation of Embodiment 2 of the ultrasound diagnostic image data processing method according to the present invention will be described.

Figure 9:
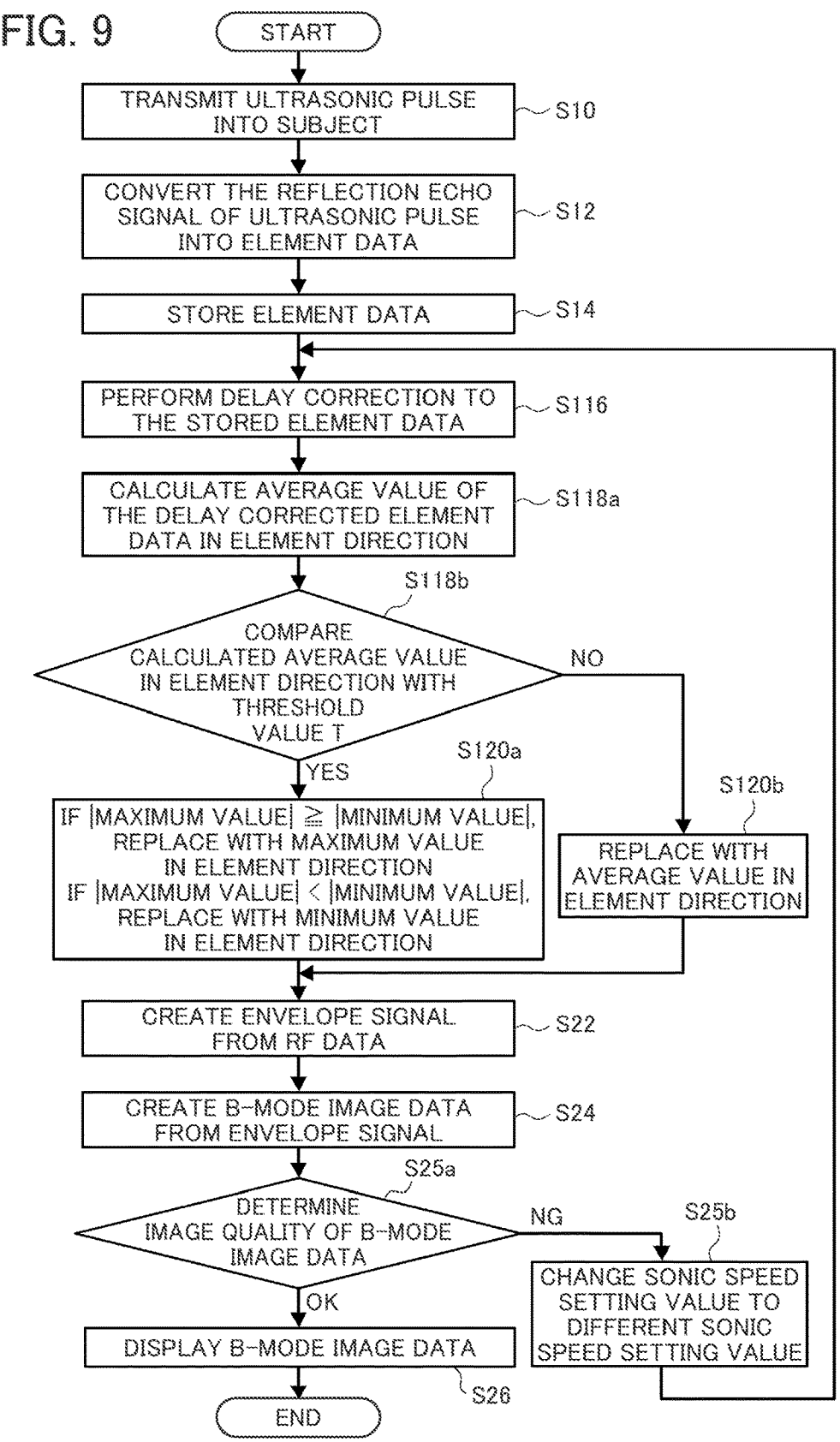
FIG. 9 is a flowchart showing Embodiment 2 of a procedure of an ultrasound diagnostic image data processing method according to the present invention.

FIG. 9 is a flowchart showing Embodiment 2 of a procedure of an ultrasonic diagnostic image data processing method according to the present invention. Embodiment 2 further includes Step S25a between Step S24 and Step S26 shown in FIG. 7. If the determination result in Step S25 is "OK", the process proceeds to Step S26 similarly to Embodiment 1, and if the determination result is "NG", the process returns to Step S116 of Embodiment 1 through Step S25b.

Other parts are the same as Embodiment 1 of the ultrasound diagnostic image data processing method according to the present invention shown in FIG. 7.

In Step S25a, the image quality determining unit 21 determines the image quality of the B-mode image data created in Step S24, in response to the amount of image features of the ultrasound image.

In Step S25b, if the image quality determining unit 21 determines that the image quality of the B-mode image data does not satisfy the image quality criteria in Step S25a, the process condition changing unit 24 changes the sonic speed setting value currently set to a different sonic speed setting value. In that case in which the image quality of the B-mode image data is determined not to satisfy the image quality criteria, a series of procedures including, changing the sonic speed setting value by Step S25b, element data delay time correction by Step S116, determining the quality of the element data by Steps S118a, and S118b, creating an ultrasound image by Steps S120a, S120b, S22, and S24, and determining the image quality of the ultrasound image by Step S25a, is controlled to be repeated, until the image quality determining unit 21 determines that the image quality of the B-mode image data satisfies the image quality criteria, in Step S25a.

Meanwhile, delay correction on the element data in the case the sonic speed setting value is changed will be described.

Figure 10:
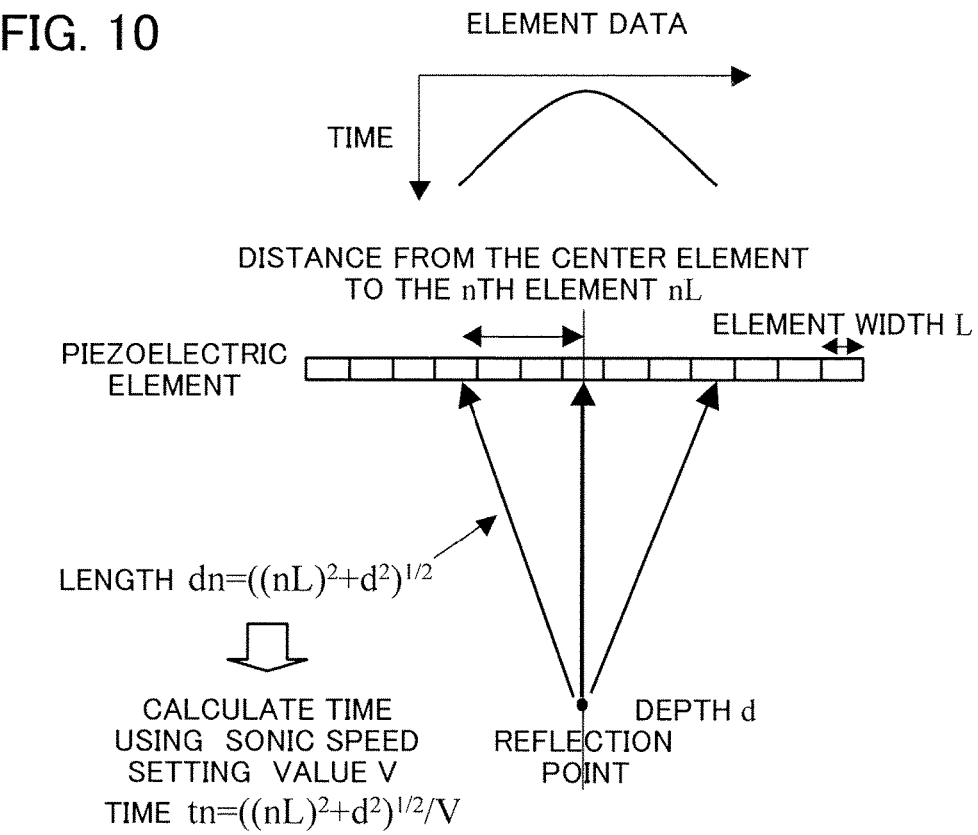
FIG. 10 is a schematic diagram illustrating how delay correction is performed to the element data based on a sonic speed setting value.
Figure 11:
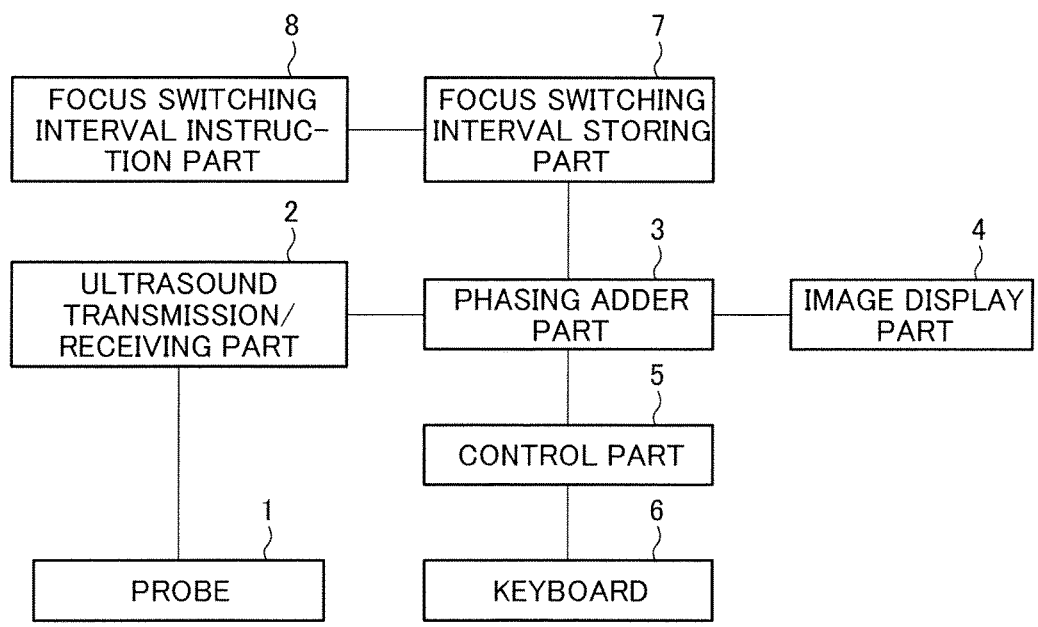
FIG. 11 is a block diagram showing a prior art ultrasound diagnostic apparatus.

FIG. 10 is a schematic diagram illustrating how delay correction is performed on the element data based on a sonic speed setting value. As shown in FIG. 10, a case in which a plurality of piezoelectric elements of the ultrasound probe are arranged in a line in the horizontal direction is considered.

Assuming the width of each piezoelectric element of the piezoelectric elements in the arranging direction is as L, the distance from the center piezoelectric element to the nth piezoelectric element in the arranging direction toward the end part will be nL.

As shown in FIG. 10, assuming that the reflection point of the ultrasonic wave exists at a distance (depth) d vertical to the arranging direction and from the center piezoelectric element, a distance (length) $d_n$ between the nth piezoelectric element and the reflection point is calculated in equation (1):

$$d_n = ((nL)^2 + d^2)^{1/2} \quad (1)$$

Thus, using the sonic speed setting value V, the time $t_n$ until the ultrasonic wave from the reflection point is received by the nth piezoelectric element can be calculated in equation (2):

$$t_n = d_n/V = ((nL)^2 + d^2)^{1/2}/V \quad (2)$$

As described above, since the distance between each piezoelectric element and the reflection point varies, and in this case, as shown in the upper graph in FIG. 10, the time $t_n$ becomes longer as the piezoelectric element is closer to the ends in the arranging direction.

That is, assuming that the time until the ultrasonic wave from the reflection point is received by the nth piezoelectric element is t1, the ultrasonic wave received by the nth piezoelectric element delays from the ultrasonic wave received by the center piezoelectric element by a time $\Delta t = t_n - t_1$. The delay correction unit 160 corrects such delay time represented by time $\Delta t$ as described above for the element data corresponding to each piezoelectric element. Such delayed delay time $\Delta t$ is called as a reception delay pattern. As described above, the delay time $\Delta t$ for the element data of each piezoelectric element is calculated from the distance obtained from the geometric arrangement of the reflection point and the piezoelectric element, and the sonic speed setting value.

It should be noted that although in the above example, the ultrasound probe is a linear probe, a convex probe may also be used based on the same idea, except that the probe shape is different.

Embodiment 2 of the ultrasound diagnostic image data processing method according to the present invention is basically configured by the above steps.

Although the ultrasound diagnostic apparatus according to the present invention has been described heretofore in detail referring to embodiments and examples, it should be appreciated that the present invention is not limited to the foregoing embodiments and examples, and various improvement or changes may be made without departing from the gist of the invention.

For example, the sonic speed setting value to be initially set by the delay correction unit 160 may not be a predetermined value, but may be input each time by an operator through a not shown input means. In addition, the threshold value T, with which the element data determining unit 164 compares the average value Aa, or Ab of the amplitude values in the element direction of the element data, may not be a predetermined value, but may be input each time by an operator through a not shown input means. In addition, the image quality criteria with which the image quality determining unit 21 determines the image quality of the B-mode image data may not be a predetermined value, but may be input each time by an operator through a not shown input means.

Further, when, for the ultrasound image being determined not to be of predetermined image quality, a series of procedures including, changing the sonic speed setting value, delay time correction of the element data, determining the quality of the element data, creating the ultrasound image, and determining the image quality of the ultrasound image is repeated until the ultrasound image corresponding to the B-mode image data created by the image producing unit 20, is determined to be of a predetermined quality by the image quality determining unit 21, the number of repetitions may be controlled to prevent the repetition continues forever. For example, the maximum number of repetitions is predetermined, and when the actual number of repetitions reaches the predetermined maximum number value, the ultrasonic wave diagnostic image data processing is automatically terminated, as well as the operator is informed of such forced termination.

The ultrasound diagnostic apparatus and the ultrasound diagnostic image data processing method of the present invention are industrial applicable because of the excellent S/N, as well as the capability of displaying an ultrasound image adjusted to an optimum focus.

What is claimed is:
1. An ultrasound diagnostic apparatus, comprising:

an ultrasound probe having an ultrasound transmitter/receiver configured to transmit an ultrasonic pulse to a subject by using a plurality of ultrasound transmitting/receiving elements arranged in one direction, and to receive an ultrasonic echo that is the ultrasonic pulse reflected by the subject, to produce an element data;

an element data storage configured to store the element data produced by the ultrasound transmitter/receiver; and a processor, the processor configured:

to correct, by a delay correcting function, a delay time of the element data of the plurality of ultrasound transmitting/receiving elements in an arranging direction of the one direction by using a predetermined sonic speed setting value, to perform phasing on the element data, the delay time being an arrival time difference of the ultrasonic echo in the element data read out from the element data storage;

to determine, by an element data determining function, a quality of the element data, based on a distribution of amplitude values of the element data after correction of the delay time of the plurality of ultrasound transmitting/receiving elements in the arranging direction of the one direction, the quality of the element data being susceptible to a noise in the element data; and to produce, by an image producing function, an ultrasound image, by performing different processes on the element data in response to a determination result from the element data determining function, wherein the element data determining function compares an average value of amplitude values of the element data with a threshold value predetermined in response to the noise, without phasing addition after correction of the delay time of the plurality of ultrasound transmitting/receiving elements in the arranging direction of the one direction, and if the average value is greater than the threshold value, the element data determining function determines that the element data is of high quality with influence of the noise reduced, or if the average value is equal to or lower than the threshold value, the element data determining function determines that the element data is of low quality due to influence of the noise, wherein, if the element data determining function determines that the element data is of high quality, the image producing function further compares an absolute value of a maximum value with an absolute value of a minimum value, out of the amplitude values of the element data after correction of the delay time of the plurality of ultrasound transmitting/receiving elements in the arranging direction of the one direction, and produces the ultrasound image respectively, if the absolute value of the maximum value is equal to or greater than the absolute value of the minimum value, with use of the maximum value of the amplitude values in the element arranging direction of the element data, or if the absolute value of the maximum value is less than the absolute value of the minimum value, with use of the minimum value of the amplitude values in the element arranging direction of the element data, and if the element data determining function determines that the element data is of low quality, the image producing function produces the ultrasound image with use of the average value of all the amplitude values of the element data after correction of the delay time of the plurality of ultrasound transmitting/receiving elements in the arranging direction of the one direction.

2. The ultrasound diagnostic apparatus according to claim 1, the processor further configured to determine, by an image quality determining function, the image quality of the ultrasound image produced by the image producing function, in response to a value of image features of the ultrasound image.

3. The ultrasound diagnostic apparatus according to claim 2, wherein the image quality determining function determines the image quality of the ultrasound image produced by the image producing function, on the basis of a brightness value of the ultrasound image.

4. The ultrasound diagnostic apparatus according to claim 2, wherein the image quality determining function determines the image quality of the ultrasound image produced by the image producing function, on the basis of a sharpness value of the ultrasound image.

5. The ultrasound diagnostic apparatus according to claim 2, wherein the image quality determining function determines the image quality of the ultrasound image produced by the image producing function, in response to whether the amount of image features is equal to or greater than a threshold value corresponding to a predetermined level of image quality of an ultrasound image, or not.

6. The ultrasound diagnostic apparatus according to claim 2, the processor further configured to change, by a process condition changing function, the sonic speed setting value if the image quality determining function determines that the ultrasound image produced by the image producing function does not have predetermined image quality, wherein, if the image quality determining function determines that the ultrasound image produced by the image producing function does not have predetermined image quality, changing the sonic speed setting value by the process condition changing function, correcting the delay time of the element data by the delay correcting function, determining the quality of the element data by the element data determining function, producing the ultrasound image by the image producing function, and determining the image quality of the ultrasound image by the image quality determining function are controlled to be repeated, until the image quality determining function determines that the ultrasound image has the predetermined image quality.

7. An ultrasound diagnostic image data processing method, comprising:

a first step of producing an element data by transmitting an ultrasonic pulse from a plurality of ultrasound transmitting/receiving elements arranged in one direction to a subject, and receiving an ultrasonic echo which is the ultrasonic pulse transmitted and reflected by the subject by the plurality of ultrasound transmitting/receiving elements;

a second step of storing the element data produced in the first step in an element data storage;

a third step of correcting a delay time of the element data of the plurality of ultrasound transmitting/receiving elements in an arranging direction of the one direction, by using a predetermined sonic speed setting value to perform phasing on the element data, the delay time being an arrival time difference of the ultrasonic echo in the element data read out from the element data storage;

a fourth step of determining a quality of the element data which is susceptible to a noise in the element data, based on a distribution of amplitude values of the element data after correction of the delay time of the plurality of ultrasound transmitting/receiving elements in the arranging direction of the one direction; and a fifth step of producing an ultrasound image by performing different processes on the element data, in response to a determination result of the element data quality in the fourth step, wherein in the fourth step, an average value of amplitude values of the element data is compared with a threshold value predetermined in response to the noise, without phasing addition after correction of the delay time of the plurality of ultrasound transmitting/receiving elements in the arranging direction of the one direction, and if the average value is greater than the threshold value, it is determined that the element data is of high quality with influence of the noise reduced, or if the average value is equal to or lower than the threshold value, it is determined that the element data is of low quality due to influence of the noise, wherein in the fifth step, if it is determined that the element data is of high quality in the fourth step, an absolute value of a maximum value are further compared with an absolute value of a minimum value, out of the amplitude values of the element data after correction of the delay time of the plurality of ultrasound transmitting/receiving elements in the arranging direction of the one direction, and the ultrasound image is produced respectively, if the absolute value of the maximum value is equal to or greater than the absolute value of the minimum value, with use of the maximum value of the amplitude values in the element arranging direction of the element data, or if the absolute value of the maximum value is less than the absolute value of the minimum value, with use of the minimum value of the amplitude values in the element arranging direction of the element data, and if it is determined that the element data is of low quality, the ultrasound image is produced with use of the average value of all the amplitude values of the element data after correction of the delay time of the plurality of ultrasound transmitting/receiving elements in the arranging direction of the one direction.

8. The ultrasound diagnostic image data processing method according to claim 7, further comprising:

a sixth step of determining the image quality of the ultrasound image produced in the fifth step, in response to a value of image features of the ultrasound image; and a seventh step of changing the sonic speed setting value if the ultrasound image produced in the fifth step is determined not to be of predetermined image quality in the sixth step, wherein, if the ultrasound image is determined not to be of predetermined image quality, changing the sonic speed setting value in the seventh step, correcting the delay time of the element data in the third step, determining the quality of the element data in the fourth step, producing the ultrasound image in the fifth step, and determining the image quality of the ultrasound image in the sixth step are controlled to be repeated, until the ultrasound image is determined to be of the predetermined image quality.

9. The ultrasound diagnostic image data processing method according to claim 8, wherein in the sixth step, the image quality of the ultrasound image produced in the fifth step is determined on the basis of a brightness value of the ultrasound image.

10. The ultrasound diagnostic image data processing method according to claim 8, wherein in the sixth step, the image quality of the ultrasound image produced in the fifth step is determined on the basis of a sharpness value of the ultrasound image.

11. The ultrasound diagnostic image data processing method according to claim 8, wherein in the sixth step, the image quality of the ultrasound image produced in the fifth step is determined in response to whether the amount of image features is equal to or greater than a threshold value corresponding to a predetermined level of image quality of an ultrasound image, or not.

* * * * *